United States Patent

Karkantis et al.

Patent Number: 5,372,782
Date of Patent: Dec. 13, 1994

[54] AUTOMATED SAMPLING DEVICE FOR MEDICAL DIAGNOSTIC INSTRUMENT

[75] Inventors: Peter N. Karkantis, Acton; Beat R. Degen, Bellingham; Richard A. Dussault, Attleboro; Richard L. Schulkind, Sharon; Norman K. Parker, Northfield, all of Mass.

[73] Assignee: Ciba Corning Diagnostics Corp., Medfield, Mass.

[21] Appl. No.: 891,553

[22] Filed: May 29, 1992

[51] Int. Cl.$^5$ .................. G01N 33/48; G01N 35/02
[52] U.S. Cl. .................. 422/63; 422/100; 604/206; 436/48; 436/49
[58] Field of Search ............ 422/63, 64, 100; 604/122, 192, 206; 436/48, 49

[56] References Cited

U.S. PATENT DOCUMENTS

| | | | |
|---|---|---|---|
| 3,989,044 | 11/1976 | Meierhoefer | 604/192 |
| 4,325,909 | 4/1982 | Coulter et al. | 422/100 X |
| 4,434,672 | 3/1984 | Williamson et al. | 73/864.22 |
| 4,439,674 | 3/1984 | Amberny et al. | 250/227 |
| 4,454,418 | 6/1984 | Walker | 250/227 |
| 4,820,497 | 4/1989 | Howell | 422/63 |
| 4,927,603 | 5/1990 | Fischer et al. | 422/67 |
| 4,935,010 | 6/1990 | Cox et al. | 604/122 |
| 4,962,041 | 10/1990 | Roginski | 422/63 X |
| 5,012,845 | 5/1991 | Averette | 422/63 X |
| 5,032,361 | 7/1991 | Kleinhappl et al. | 422/67 |
| 5,035,704 | 7/1991 | Lambert et al. | 606/182 |

Primary Examiner—James C. Housel
Assistant Examiner—Milton I. Cano
Attorney, Agent, or Firm—Arthur S. Morgenstern; Nicholas I. Slepchuk, Jr.; Judith A. Roesler

[57] ABSTRACT

A novel fluid sampling device has been developed. This device provides for sample entry to be handled automatically by the instrument, thus allowing the operator to be involved in other activities while the sampling process is underway. It also assures reproduceable sample size, automatically cleans the sampling device between samples, and reduces the risk of user injury. Furthermore, the sampling system allows for the use of any forseeable collection mechanism.

1 Claim, 4 Drawing Sheets

AUTOMATED SAMPLING DEVICE FOR MEDICAL DIAGNOSTIC INSTRUMENT

BACKGROUND

This invention relates to a device which is used for sampling fluids which are to be analyzed by a laboratory instrument. Although many applications are contemplated, the one used to describe the operation of the device is for analysis of sampled blood. The blood is normally collected by using a syringe to draw the blood or by collecting the blood in a glass capillary tube.

The currently available analytical instruments use three methods of delivering the blood sample to the instrument. First, if a syringe is used, the sample might be injected into the instrument sampling port. There is much variability in this approach, due to the fact that (1) the force used to inject the sample may vary from operator to operator, (2) the force used to inject the sample into the instrument may vary from test to test, (3) the force may vary throughout the injection of a single sample, and (4) the sample size may vary from test to test.

Second, some instruments aspirate the sample from the syringe. For these instruments to be operable, a sampling probe protruding from the instrument must be manually aligned with the syringe carrying the blood. This approach takes much time, demands manual dexterity on the part of the user, requires cleaning the probe after each use to avoid cross-contamination of samples, risks skin puncture of the technician by the probe, and risks exposure of the technician to blood overflow.

Third, if the sample is introduced via a capillary, it is necessary in some instruments to attach a special adaptor to the capillary so that the sample can be drawn from the capillary by a vacuum drawn by the instrument. This requires time to connect the adaptor, risks exposure of the technician to potentially contaminated blood, and requires manual cleaning or disposal of equipment, including the adaptor. In some instruments the operator is forced to hold and maintain a seal with the sample entry throughout the aspiration process.

Summary of Invention

A novel fluid sampling device has been developed. This device provides for sample entry to be handled automatically by the instrument, thus allowing the operator to be involved in other activities (such as monitoring other instruments, etc.) while the sampling process is underway. It also assures reproduceable sample size, automatically cleans the sampling device between samples, and reduces the risk of user injury from innoculation by the probe. Furthermore, the sampling system allows for the use of any forseeable collection mechanism.

DETAILS OF THE INVENTION

A novel sampling device, intended primarily for use in handling blood samples to be analyzed in medical diagnostics instruments, has been developed. This sampling device also has utility in other applications where liquid, gaseous, solid or mixed-phase (e.g., suspensions, such as blood or plasma) samples are drawn. Examples of other instruments where the device could show utility include analytical chemistry instruments, air sampling and analysis instruments, food sampling instruments, etc.).

For the purpose of this invention, the mechanism involved in sensing the type of container holding the sample, drawing the sample from the container, cleaning the portions of the mechanism exposed to sample, and related activities is referred to collectively as the device. Portions of the device are referred to as systems. The entire mechanism, including the "device" and the portion which analyzes the sample drawn, is referred to as the instrument.

The main attributes of the sampling device are that:
1. sampling is handled automatically so that the operator can be freed to perform other tasks while the sampling is taking place,
2. samples can be drawn from a variety of container types,
3. a reproduceable sample size is drawn (including a reproduceable rate of drawing the sample),
4. the sampling device is automatically and effectively washed after each sample is drawn, and
5. user safety is improved.

Figure 1:
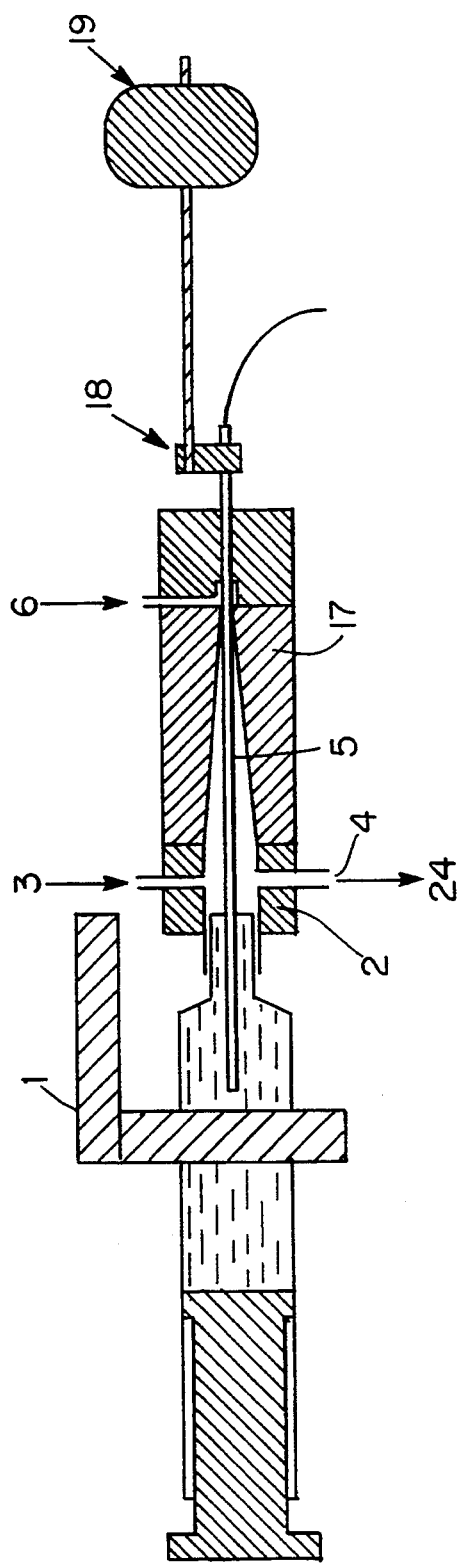
FIG. 1 represents the sampling device during the process of drawing a sample from a syringe.
Figure 5:
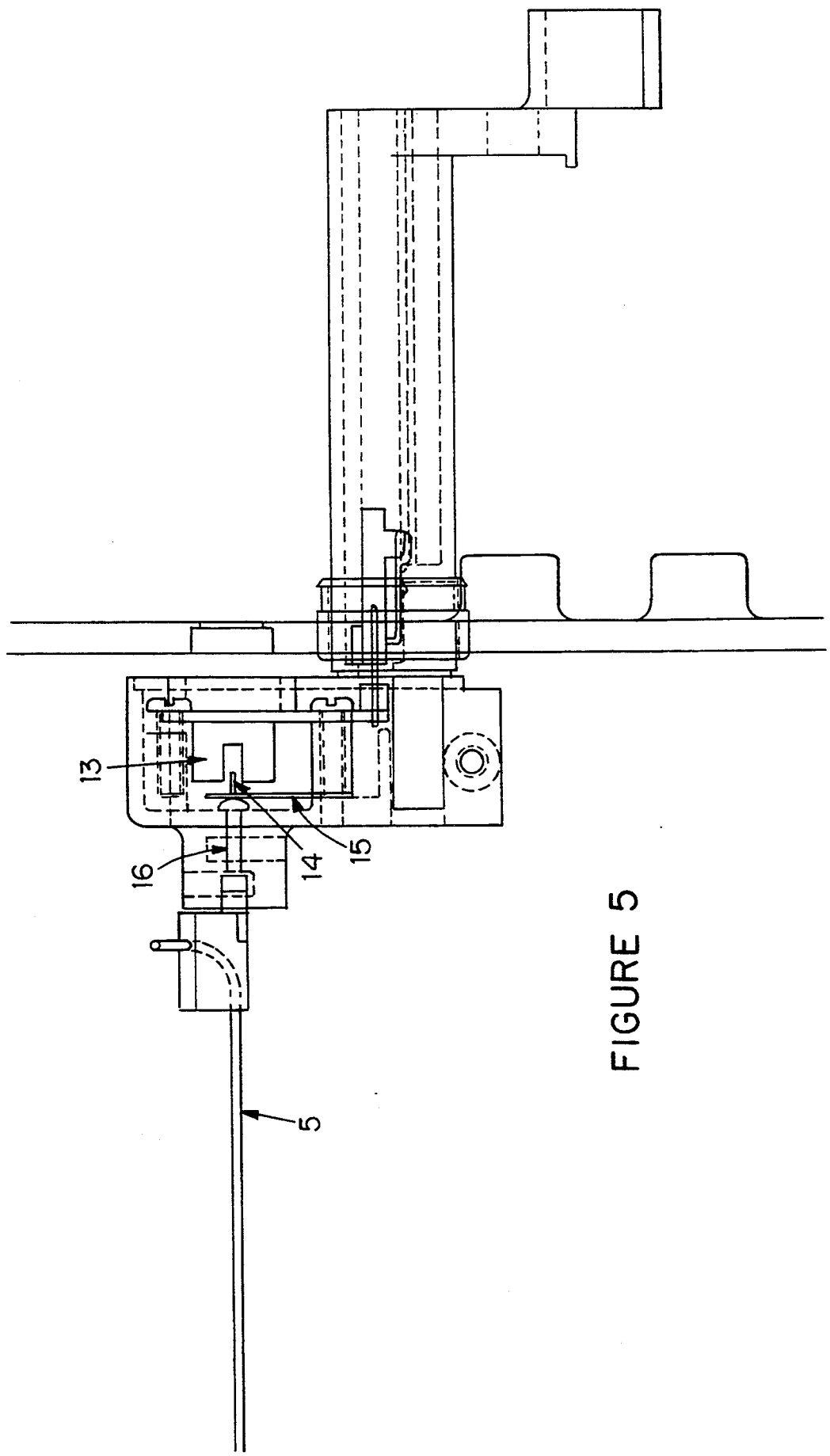
FIG. 5 represents the probe obstruction detection system.

FIG. 1 shows a schematic of the sampling device with a syringe as the sample holder. 1 represents the "smart door", 2 represents the sample entry Luer, 3 is the inlet for the wash solution, 4 is the outlet for pumped waste, 5 is the probe, and 6 is the gas and reagent port (where standardizing gas and liquid samples are drawn into the instrument and overflow sample is allowed to escape). 17 represents the capillary seal through which the probe is moved and which forms a seal with the probe. It also creates a seal with the inserted capillary. 18 represents the probe obstruction detection system, to be discussed further in reference to FIG. 5, and 19 represents the linear bidirectional actuator, which moves the probe into a syringe.

The sample entry Luer is tapered using the ANSI/HIMA MD70.1-1983 standard taper that is used on all syringes, and contains the gas and reagent port referred to above (item 6). The syringe, without its needle, is held tightly by friction against the female Luer taper, and the sampling device automatically draws the sample, thus freeing the technician to perform other tasks while the sampling takes place.

The Luer can be made of any material that will hold the syringe in the desired orientation and will not contaminate the sample, for example polyethylene, stainless steel, silicone, urethane, TEFLON (polytetrafluoroethylene), and preferably clear acrylic, for example POLYCAST (polymethal-methacrolyte), made by Rohm and Haas, or PERSPEX (methacrylic acid) made by ICI. The acrylic PMMA (polymethylmethacrylate) has the added benefit of making the Luer transparent. All standard types of syringes will fit into the Luer, although it is most likely that syringes holding between 1 cc and 30 cc will be used.

Figure 2:
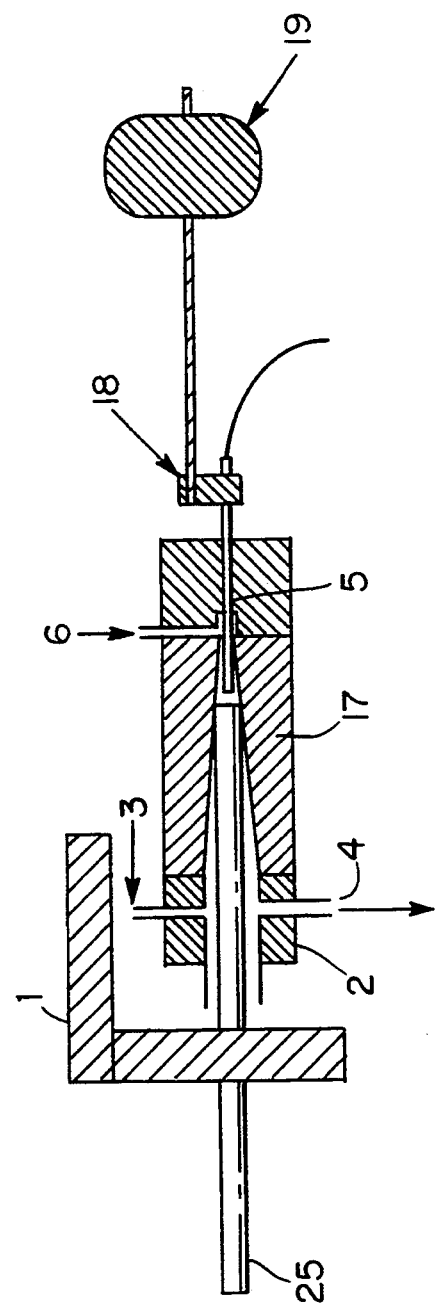
FIG. 2 represents the sampling device drawing a sample from a capillary.

It should be noted that capillaries that are used to collect blood samples will also fit into the sample entry system and the preferred embodiment is one in which the capillary will be firmly held in a horizontal position in the capillary seal. (See FIG. 2, where item 25 represents the capillary.) The capillary seal is designed to have a conical shape in order to hold all the different capillary sizes. The capillary seal can be made of any material that is flexible enough to hold and seal the capillary and the sample probe. The material must also not contaminate the sample. For example, thermoset rubbers, such as silicon (for example, GE 4404 43-50 shore A durometer), and thermoplastic rubbers, such as KRAYTON (SBR Rubber) G or D (from Shell), can be used. Because of the capillary seal design, all forseeable diameters of capillaries can be used, although the most common are expected to be between 50 and 175 $\mu$l volume.

The materials discussed above hold the syringe, capillary or other sample container in the Luer or capillary seal primarily by frictional forces between the sample container and the Luer. Alternatively, a material or design that does not cause the sample container to be held by friction can be used, but in that case a different mechanism for holding the sample container in the Luer must be included.

It should also be noted that, due to the uniformly tapered design of the sample entry system (Luer or capillary seal), the sample container (syringe, capillary, or other container) is held rigidly in the center of the Luer and aligned concentrically with the narrow-opening end of the Luer.

When the syringe or capillary is positioned in the sample entry system, the operator presses the start switch, and the "smart door" closes by rotating about the pivot point connecting it to the device. This "smart door" is actually a moving arm which determines the type of container present by measuring the diameter thereof. The location where it stops its motion is an indicator to the device of the type of blood holding container that is being used.

The type of sample container detected indicates to the instrument how a sample is to be drawn from the sampling device. If a syringe is detected, a movable probe is inserted into the syringe to draw, in a reproduceable manner, using vacuum applied to the probe, the sample of blood from the container of blood. If a capillary is detected, a vacuum, applied to the probe in a reproduceable manner, draws the sample from the capillary. Because of the low vacuum used in the sampling pump, there is little chance that a clot will get into and clog the instrument.

After the instrument draws the sample from the syringe or other sample holder, the user is instructed to remove the sample holder, at which time the door automatically closes, blocking the Luer entry. While entry of a sample is prevented, the instrument performs the operations of analyzing the previously drawn sample, washing the Luer and sampling probe, and calibrating the instrument.

Analytical instruments currently in the marketplace provide for sample entry "straight ahead" into the instrument (i.e., the syringe or capillary points along a line going from the operator). Unexpectedly, it has been found that it is easier to utilize the novel device if there is a sidewise orientation of the sampling system, particularly if it is pointing towards the right side, when the user is facing the instrument. Not only has it been found easier for right-handed persons to use, but also, because of the ease of aligning the sample container with the Luer, it has also been found easier for left-handed persons to use. Furthermore, because the syringe (or other sample holder) no longer extends towards the operator, but rather along the instrument or over a "guard" that can easily be designed into the instrument, the syringe and sample are less likely to be accidentally jarred by the operator and knocked from the instrument.

The integration of all of the systems of the device contribute to the reduction of risk to the instrument's operator, due both to the reduction in risk of injury and in reduction in the exposure to blood. Specifically, the probe does not operate until the smart door first detects a sample collection device (i.e., syringe, capillary, etc.) inserted in the Luer; due to the ability of the probe to detect obstructions, the likelihood of its puncturing skin is negligible; the entire sampling takes place in a closed area, reducing spillage, backsplash and exposure to blood; and automatic washing of the system between samples reduces exposure due to contamination from sample residues.

Detailed descriptions of the systems referred to above follow.

Smart Door Operation

Figure 3:
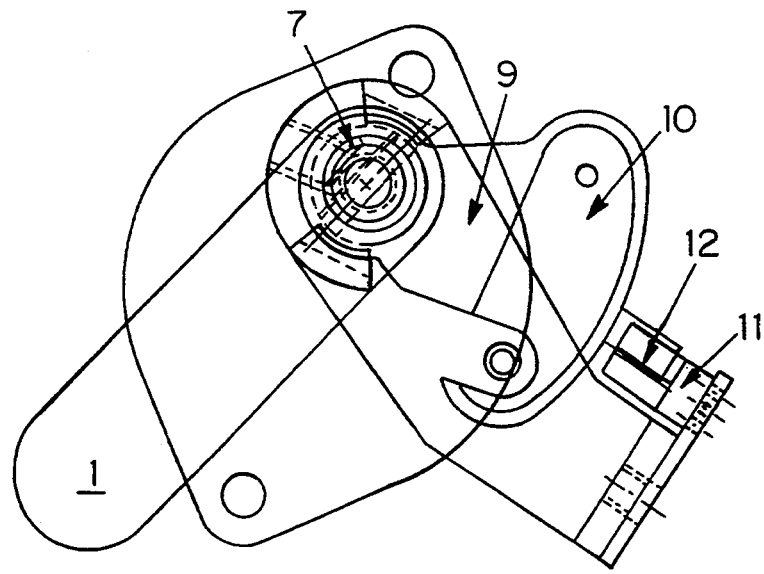
FIG. 3 represents the front view of the "smart door" system.
Figure 4:
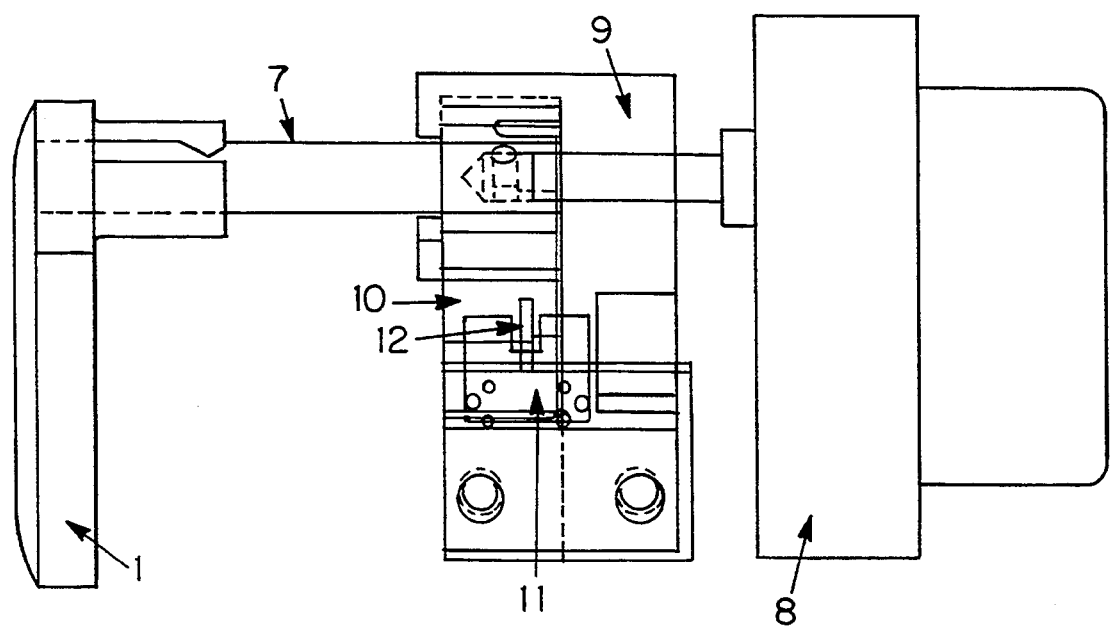
FIG. 4 represents the side view of the "smart door" system.

The Smart Door Assembly is shown in FIGS. 3 (front view) and 4 (side view). The door, 1, is coupled to a shaft, 7, that pivots about a contact point and rotates via a stepper motor, 8. The door shaft has a drive piece, 9, and a driven piece, 10. The drive piece is directly coupled to the stepper motor. The driven piece is connected (via a spring coupling) to the drive piece, and it includes the door and the optical detector, 11, for determining the stopping point for the flag, 12, on the driven piece, which has the same movement as the door.

Two locations for the door are fixed in the instrument's memory: the home, or fully opened, location and the fully closed location, and these positions are established by optical position detectors. Other locations for common types of syringes and capillaries are also programmed in the instrument. When the door is closing, the stepper motor counts the number of steps that the shaft has taken from its home position until it intercepts the sampling device. The point of interception is determined when the optical detector, 11, is tripped.

Unusual sampling devices, for example special sizes of syringes and capillaries, can be programmed into the instrument by the user.

For example, the following data might represent the table of steps for several sampling devices:

| Position/Container | Number of Steps |
| --- | --- |
| Door open | 0 |
| 30 cc syringe | 25–30 |
| 12 cc syringe | 39–40 |
| 3 cc syringe | 79–80 |
| 2 cc syringe | 89–90 |
| 1 cc syringe | 98–99 |
| 275 $\mu$l capillary | 114–115 |
| 100 $\mu$l capillary | 133–134 |
| Door closed | 175 |

Motorized Probe Operation

A probe that has a sufficiently small outside diameter (typically from 0,032–0,046 in.) so that it can fit into the various syringes being used, is employed to draw sample in a reproduceable fashion from the syringes. The sample probe can be made of metal (e.g., stainless steel, titanium, or inconel or plastic (e.g., PEEK (polyetheretherletone) (ICI America), KEL-F (chlorotrifluororthylene) (3M), etc.). Once the system detects, via the use of the "smart door", that a syringe is present, the probe is activated. The motorized probe is automatically advanced through the capillary seal into the syringe barrel and the sample is drawn into the instrument. Alternatively, the probe can remain stationary, and the syringe and Luer can move laterally until the probe is inside the syringe. When the capillary is the sample container, a vacuum system is connected to the capillary for withdrawing an aliquot of sample.

The motorized probe has the ability to sense a small obstruction at the probe tip, for example a syringe plunger, a finger, etc. As small a force as 0.25 pounds can be detected, which is less than what would be encountered in hitting intact skin. As a result, the device minimizes the chance of injuring a technician. In addition, the device adapts the sampling procedure to the volume of sample in the container, assuring that air will not be drawn into the instrument along with the sample. If the probe encounters an obstruction during its outward motion, it senses the obstruction, stops its forward motion, retracts, and the instrument displays a probe obstruction message to the user. If the system determines that too small of a sample is present, the probe will be withdrawn, and an error message will be displayed. If the instrument should fail to detect a problem and proceeds with sampling, two detectors in the sampling line assure that there is present an integral sample (i.e., the detectors determine if a bubble exists in the sample line, using, for example, a conductivity or optical measuring device). If a problem with the sample is detected, an error message is displayed.

The Probe Obstruction Detection System is shown in FIG. 5. The method of detecting the obstruction utilizes an optical detector, 13, a flag, 14, mounted on a cantilever flex beam, 15, and a push rod, 16 that is in contact with the flex beam. As the probe encounters an obstruction, the probe pushes on the push rod, the flex beam bends and the flag interrupts the optical detector's light path. By adjusting the electronic signal processing, the obstruction detection sensitivity can be increased or decreased.

Device Cleaning

Figure 6:
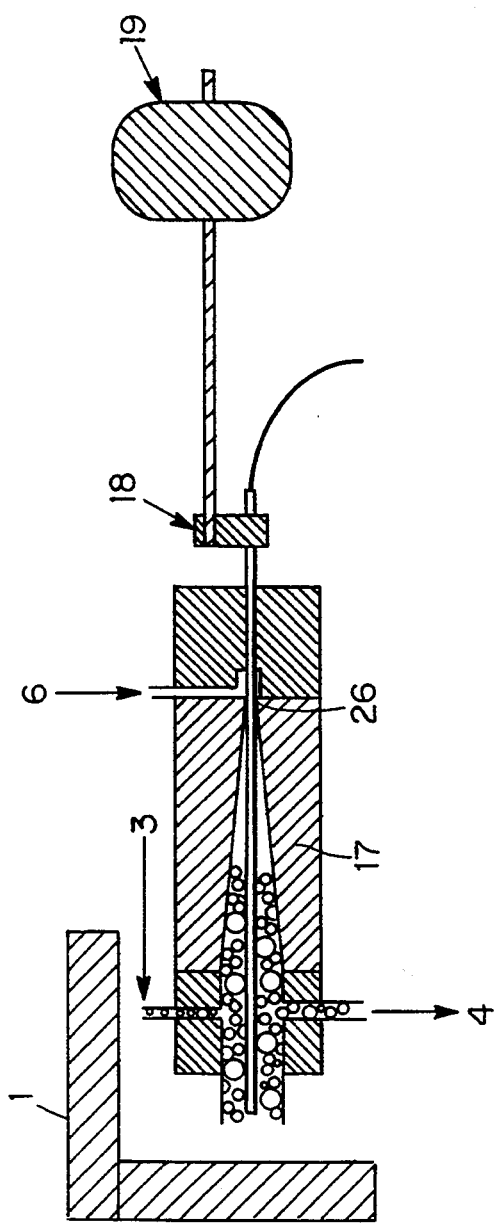
FIG. 6 represents the wash system.

The device senses when a sample or reference has been drawn and initiates the washing cycle after each material (sample or reference) has been drawn. During this washing cycle the probe, capillary conical seal, and related components are automatically cleaned to avoid contamination. It should be noted that, during each cleaning operation, the smart door is automatically closed in order to prevent the introduction of a new sample. The wash and waste fluidic paths reside within the Luer. (See FIG. 6.) The wash solution, which contains a surfactant, such as BRIJ (Polyoxyethylene 23 lauryl ether) (from ICI) or TRITON X100 (oxtoxynol-9) (from Rohm and Haas), is introduced in the Luer directly above the probe's outside surface, 3, while the probe is located in the Luer/probe wash position (see FIG. 6). The wash solution fills the Luer and capillary seal, and it surrounds the outside of the probe. The outside area of the probe that is surrounded with the foam wash solution is the area that was inserted into the syringe and thus requires washing.) The waste is collected in the Luer at the probe's outside bottom surface, 4. The outside of the probe exposed to the blood sample is washed inside the Luer without the probe coming in contact with any parts of the instrument. Once the outside of the probe is washed, the probe is withdrawn into the capillary seal, 17, where the washing of the capillary seal and interior of the probe takes place. The washing cycle takes place at the same time that the instrument's measurement cycle occurs, in order to optimize instrument throughput. In addition to the cleaning provided by the washing solution, cleaning also occurs by the wiping of the outside of the probe by the narrowest portion of the capillary seal (26) when the probe is withdrawn into its home position, which is the reagent-/gas/wash entry location (6). The narrowest portion of the capillary also provides a seal with the probe. (It should be noted that cleaning of the balance of the instrument that is exposed to sample or calibration solution is separately conducted after each such material is drawn through the instrument.)

In the preferred embodiment, even though the Smart Door does not make a seal with the Luer port, wash solution does not leak because of the properties of the foam wash solution (surface tension, etc.). In addition, the timing of the peristaltic pump, which delivers the wash solution, and the waste pump are synchronized so that there will be no excess wash solution to drip out of the Luer. Alternatively, the Smart Door could make contact with the Luer port, especially if a wash solution having other properties (e.g., a solution containing an organic solvent) were used.

The generation and delivery of foam wash into the Luer is the technique used to wash and clean the blood from the outside of the probe and the inside of the Luer. The generation of foam in a controlled manner has been found to provide cleaning in a reliable, simple and effective manner. It has been found to be more efficient, due to the fluid volume consumption and drip minimization, than systems currently used by other instruments, which involve either immersing the probe into a wash bath or manual washing of the sampling probe. In addition, the techniques used in other instruments require either expensive hardware or manual intervention.

Figure 7:
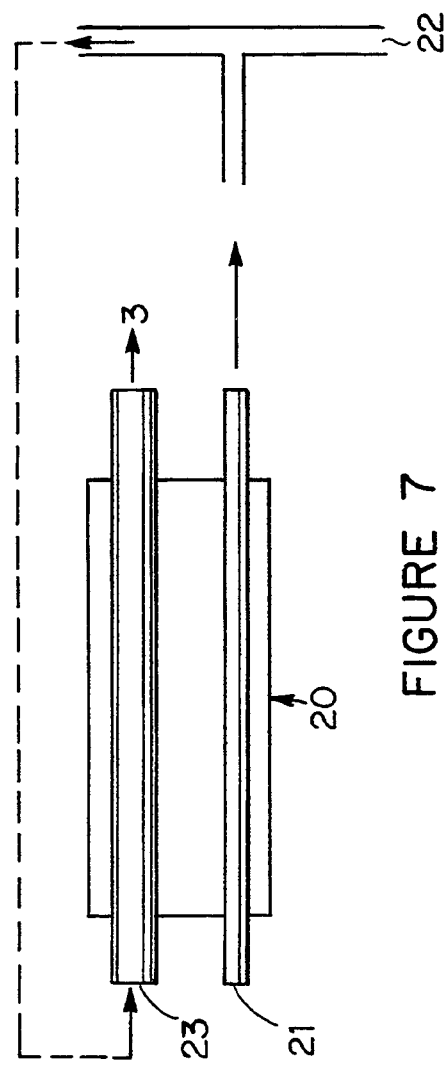
FIG. 7 represents the foam generation system.

The foam wash (see FIG. 7) is developed by having two different inside diameter size tubes (pump tubes) on a peristaltic pump, 20. The difference in the inside diameter of the tubing is required to obtain an optimum flow rate ratio of surfactant to water. The smaller diameter tube, 21, pushes wash solution into a "T" junction, 22, where the larger tube, 23, pulls air in front of the "T" junction. The liquid and air form a mixture in this "T" junction. The size of the air to liquid microsegments can be varied by changing the tubing diameters. The larger diameter tube also delivers the air/liquid mixture via the wash solution inlet (3) into the Luer, where they become foam (i.e., form a foam structure). In order to generate in the Luer foam of the desired bubble size for the preferred embodiment, the liquid segments should be smaller than 5 $\mu$l in volume and preferably about 1 $\mu$l in volume. The foam wash and waste are delivered to the waste resevoir (24 in FIG. 1) from the Luer by vacuum generated by a waste pump. Variations in the foam generation system are contemplated as a means of expanding the usefulness of the device. For example, it would be possible to increase the number of tubes and, therefore, utilize this system to mix components and create a foam from a multicomponent solution.

The above descriptions of the device and systems are not intended to limit their usefulness, and those with ordinary skill in the art will be able to envision variations which are consistent with the intended use thereof. For example, the device can be used to draw suspensions such as liquid food samples, gas samples analyzed for occupational health monitoring, etc. These samples can then be delivered to the appropriate analytical system.

What is claimed is:

1. A device for sampling material comprising
   a. a means for detecting the presence and diameter of a container of the material,
   b. a means for withdrawing a sample of the material, wherein said withdrawing is controlled in response to the presence and diameter of the container, and
   c. a means for cleaning those parts of the device exposed to the material between the withdrawal of subsequent samples, in which said means for cleaning comprises
      a means to generate reproducible air/liquid microsegments composed of two or more pump tubes, at least 1 of which carries surfactant or a surfactant solution and at least 1 of which carries air, the diameters of said tubes being determined by the relative volume ratio of the components in the final mixture,
      a second means for allowing the components carried by the tubes to form an air/liquid reproducible mixture, and
      a third means for allowing the air/liquid mixture to form a foam due to the increased surface area of said third means.

* * * * *